(12) United States Patent
Bornert et al.

(10) Patent No.: US 9,170,313 B2
(45) Date of Patent: Oct. 27, 2015

(54) CORONARY MAGNETIC RESONANCE ANGIOGRAPHY WITH SIGNAL SEPARATION FOR WATER AND FAT

(75) Inventors: Peter Bornert, Hamburg (DE); Kay Nehrke, Ammersbek (DE); Mariya Doneva, Lubeck (DE)

(73) Assignee: Koninklijke Philips N.V., Eindhoven (NL)

( * ) Notice: Subject to any disclaimer, the term of this patent is extended or adjusted under 35 U.S.C. 154(b) by 296 days.

(21) Appl. No.: 13/575,964

(22) PCT Filed: Feb. 7, 2011

(86) PCT No.: PCT/IB2011/050504
§ 371 (c)(1),
(2), (4) Date: Jul. 30, 2012

(87) PCT Pub. No.: WO2011/098941
PCT Pub. Date: Aug. 18, 2011

(65) Prior Publication Data
US 2012/0301000 A1    Nov. 29, 2012

(30) Foreign Application Priority Data
Feb. 9, 2010    (EP) .................. 10153028.5

(51) Int. Cl.
*G06K 9/00* (2006.01)
*G01R 33/48* (2006.01)
*G01N 24/08* (2006.01)
*G01R 33/561* (2006.01)
*G01R 33/563* (2006.01)
*G01R 33/56* (2006.01)

(52) U.S. Cl.
CPC ......... *G01R 33/4828* (2013.01); *G01N 24/082* (2013.01); *G01R 33/4824* (2013.01); *G01R 33/5614* (2013.01); *G01R 33/5635* (2013.01); *G01R 33/5608* (2013.01); *G01R 33/5611* (2013.01); *G01R 33/5616* (2013.01); *G01R 33/5617* (2013.01)

(58) Field of Classification Search
USPC .................................. 382/128–134
See application file for complete search history.

(56) References Cited

U.S. PATENT DOCUMENTS

| 4,949,042 | A | * | 8/1990 | Kuhara et al. | 324/311 |
| 5,051,699 | A | * | 9/1991 | Hanawa et al. | 324/309 |
| 5,627,469 | A | * | 5/1997 | Hong et al. | 324/309 |
| 6,016,057 | A | * | 1/2000 | Ma | 324/309 |
| 6,263,228 | B1 | * | 7/2001 | Zhang et al. | 600/409 |
| 6,459,922 | B1 | * | 10/2002 | Zhang | 600/410 |
| 6,603,990 | B2 | * | 8/2003 | Zhang et al. | 600/410 |

(Continued)

OTHER PUBLICATIONS

Akcakaya, M., et al.; Accelerated coronary MRI using compressed sensing with transform domain dependencies: a feasibility study; 2010; Journal of Cardiovascular Magnetic Resonance; 12(1)36-37.

(Continued)

*Primary Examiner* — Alex Liew

(57) ABSTRACT

The invention relates to a method of performing coronary magnetic resonance angiography with signal separation for water and fat, the method comprising: acquiring coronary magnetic resonance angiography datasets using multi-echo Dixon acquisition, processing (314; 316; 318) the datasets for reconstruction of a first (320) and second (322) image data set, the first and second image data set comprising separate water and fat image data, wherein the processing of the datasets comprises a Dixon reconstruction technique.

8 Claims, 2 Drawing Sheets

(56) References Cited

U.S. PATENT DOCUMENTS

| | | | | |
|---|---|---|---|---|
| 2003/0060697 A1* | 3/2003 | Zhang et al. | | 600/410 |
| 2004/0167390 A1* | 8/2004 | Alexander et al. | | 600/410 |
| 2010/0239149 A1* | 9/2010 | Wang et al. | | 382/131 |
| 2011/0274331 A1* | 11/2011 | Weng | | 382/131 |

OTHER PUBLICATIONS

Boernert, P., et al.; Fast Single Breath-hold 3D Abdominal Spiral Imaging with Water/Fat Separation and Off-resonance Correction; 2009; Proc. Intl. Soc. Mag. Reson. Med.; 17:2148.

Doneva, M., et al.; CS-Dixon: Compressed Sensing for Water-Fat Dixon Reconstruction; 2010; Joint Annual Mtg. ISMRM-ESMRMB; p. 2919.

Goldfarb, J. W., et al.; Myocardial Fat Deposition after Left Ventricular Myocardial Infarction: Assessment by Using MR Water-Fat Separation Imaging; 2009; Radiology; 253(1)65-73.

Hernando, D., et al.; Joint Estimation of Water/Fat Images and Field Inhomogeneity Map; 2008; MRM; 59:571-580.

Johnson, K. M., et al.; Phase Contrast MRA with Simultaneous Fat-Water Separation; 2008; Proc. Intl. Soc. Mag. Reson. Med.; 16:646.

Kellman, P., et al.; Multiecho Dixon Fat and Water Separation Method for Detecting Fibrofatty Infiltration in the Myocardium; 2009; MRM; 61:215-221.

Li, D., et al.; Coronary Arteries: Three-dimensional MR Imaging with Fat Saturation and Magnetization Transfer Contrast; 1993; Radiology; 187:401-406.

Li, Z., et al.; Rapid Water and Lipid Imaging with T2 Mapping Using a Radial Ideal-Grase Technique; 2009; MRM; 61:1415-1424.

Lustig, M., et al.; Sparse MRI: The Application of Compressed Sensing for Rapid MR Imaging; 2007; MRM; 58:1182-1195.

Nehrke, K., et al.; Free-Breathing Whole-Heart Coronary MR Angiography on a Clinical Scanner in Four Minutes; 2006; Journal of Magnetic Resonance Imaging; 23:752-756.

Reeder, S. B., et al.; Multicoil Dixon Chemical Species Separation with an Iterative Least-Squares Estimation Method; 2004; MRM; 51:35-45.

Shah, S., et al.; 3T Coronary MRA using 3D Multi-interleaved Multi-echo Acquisition and VARPRO Fat-water Separation; 2010; Joint Annual Mtg. ISMRM-ESMRMB; p. 3667.

Shah, S., et al.; Coronary MRA at 3T using 3d multi-interleaved multi-echo acquisition with varpro fat-water separation; 2010; Journal of Cardiovascular Magnetic Resonance; 12(1)42-44.

Weber, O. M., et al.; Whole-Heart Steady-State Free Precession Coronary Artery Magnetic Resonance Angiography; 2003; MRM; 50:1223-1228.

Boernert, P., et al.; Direct Comparison of 3D Spiral vs. Cartesian Gradient-Echo Coronary Magnetic Resonance Angiography; 2001; MRM; 46:789-794.

Burke, A. P., et al.; Arrhythmogenic Right Ventricular Cariomyopathy and Fatty Replacement of the Right Ventricular Myocardium: Are They Different Diseases?; 1998; Circulation; 97:1571-1580.

Goldfarb, J. W.; Fat-Water Separated Delayed Hyperenhanced Myocardial Infarct Imaging; 2008; MRM; 60:503-509.

Kim, W. Y., et al.; Coronary Magnetic Resonance Angiography for the Detection of Coronary Stenoses; 2001; The New England Journal of Medicine; 345(26)1863-1869.

Man, L-C, et al.; Multifrequency Interpolation for Fast Off-resonance Correction; 1997; MRM; 37:785-792.

Moriguchi, H., et al.; Dixon Techniques in Spiral Trajectories with Off-resonance Correction: A New Approach for Fat Signal Suppression without Spatial-Spectral RF Pulses; 2003; MRM; 50:915-924.

* cited by examiner

CORONARY MAGNETIC RESONANCE ANGIOGRAPHY WITH SIGNAL SEPARATION FOR WATER AND FAT

FIELD OF THE INVENTION

The invention relates to a method of performing coronary magnetic resonance angiography with signal separation for water and fat, a computer program product, as well as a magnetic resonance imaging apparatus for performing coronary magnetic resonance angiography with signal separation for water and fat.

BACKGROUND OF THE INVENTION

Image-forming MR methods which utilize the interaction between magnetic field and nuclear spins in order to form two-dimensional or three-dimensional images are widely used nowadays, notably in the field of medical diagnostics, because for the imaging of soft tissue they are superior to other imaging methods in many respects and do not require ionizing radiation and they are usually not invasive.

According to the MR method in general, the body of a patient or in general an object to be examined is arranged in a strong, uniform magnetic field $B_0$ whose direction at the same time defines an axis, normally the z-axis, of the coordinate system on which the measurement is based. The magnetic field produces different energy levels for the individual nuclear spins in dependence on the applied magnetic field strength which spins can be excited (spin resonance) by application of an alternating electromagnetic field (RF field) of defined frequency, the so called Larmor frequency or MR frequency. From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicularly to the z-axis, so that the magnetization performs a precessional motion about the z-axis.

Any variation of the magnetization can be detected by means of receiving RF antennas, which are arranged and oriented within an examination volume of the MR device in such a manner that the variation of the magnetization is measured in the direction perpendicularly to the z-axis.

In order to realize spatial resolution in the body, linear magnetic field gradients extending along the three main axes are superposed on the uniform magnetic field, leading to a linear spatial dependency of the spin resonance frequency. The signal picked up in the receiving antennas then contains components of different frequencies which can be associated with different locations in the body. The signal data obtained via the receiving antennas corresponds to the spatial frequency domain and is called k-space data. The k-space data usually includes multiple lines acquired with different phase encoding. Each line is digitized by collection a number of samples. A sample of k-space data is converted to an MR image, e.g. by means of Fourier transformation.

Coronary magnetic resonance angiography (CMRA) has been shown to allow accessing the status of the coronary tree or the patency of corresponding bypass grafts. Whole heart approaches, benefiting from parallel reception have also been introduced to image the entire coronary tree in a single acquisition. To improve the visibility of the coronaries in their epicardial bed, fat suppression is usually employed in CMRA.

For fat suppression basically two types of approaches are used. Chemical shift selective pre-saturation uses the principle that the longitudinal magnetization of fat is selectively excited and subsequently dephased and thus suppressed. Spatial excitation is an alternative, exciting only the resonance of interest, e.g. water, ignoring the fat. Also for other cardiac scan protocols fat is often suppressed to increase the overall image contrast.

However, the suppressed fat signal also contains helpful diagnostic information for a number of cardiac diseases. For example in myocardial infarction or in the presence of suspicious cardiac masses, the intra-myocardial fat represents an important diagnostic indicator. It was even reported that fibro-fatty infiltration of the myocardium is associated with sudden death. Thus, the fat signal and its distribution may have higher prognostic value.

To address coronary artery disease and potential myocardial fat infiltration, today basically two individual scans have to be made. However, the performance of two scans has the disadvantage that it takes a rather long period of time in order to perform the scans.

An alternative way to obtain both information on water and fat contributions to the MR signal is chemical shift encoding, in which an additional dimension to the measurement data is defined and encoded, by performing a couple of additional image data acquisitions with slightly different echo times. For water-fat separation these types of experiments are often called Dixon-type of measurements. By means of Dixon imaging or Dixon water/fat imaging, a water-fat separation can be obtained by calculating contributions of water and fat from two or more corresponding echoes, acquired at different echo times. Dixon imaging usually relies on the acquisition of at least two echoes to separate water and fat signals. In general these kind of separations are possible because there is a known precessional frequency difference of hydrogen in fat and water. In its simplest form, water and fat images are generated by either addition or subtraction of the 'in phase' and 'out of phase' datasets, but this approach is rather sensitive to main field inhomogeneities. More advanced water/fat Dixon separation methods allow also an estimation of the main field inhomogeneity map. In that respect these chemical shift encoding techniques can have serious advantages over the above mentioned chemical shift selective approaches which might have image quality problems in case of large main field inhomogeneities.

Consequently, chemical shift-based water-fat separation methods require the acquisition of two or more images at different echo times, which is also prolonging the total scan time. The acquisition of several images (3D) could take too long to be performed which may cause inconsistencies between images at different echo times for example due to motion artefacts in coronary imaging. Consequently, Dixon-type of measurements have rarely been used in cardiac magnetic resonance.

For example Kellmann et al, Magnetic Resonance in Medicine 61, pages 215-221, 2009 discloses a multi-echo Dixon fat and water separation method for detecting fibro-fatty infiltration in the myocardium. However, only standard inversion recovery pulse sequence have been used to detect the fatty infiltration in chronic myocardial infarction which only provides MR image data at rather limited quality which again limits the visibility of the coronaries in their epicardial bed.

From the forgoing it is readily appreciated that there is a need for an improved MR imaging method. It is consequently an object of the invention to enable MR imaging in a fast manner by providing combined information on the coronary tree as well as on potential fibro-fatty infiltration of the myocardium. Further, from the forgoing it is readily appreciated that there is a need for an improved MR imaging system and an improved computer program product adapted to carry out the method according to the invention.

SUMMARY OF THE INVENTION

In accordance with the present invention a method of performing coronary magnetic resonance angiography with signal separation for water and fat is provided, wherein the method comprises acquiring coronary magnetic resonance angiography datasets using multi-echo Dixon acquisition and processing the datasets for reconstruction of a first and second image dataset, the first and second image dataset comprising separate water and fat image data, wherein the processing of the dataset comprises a Dixon reconstruction technique.

In other words, chemical shift encoded heart CMRA type imaging is proposed that delivers after Dixon post-processing both, the coronary tree information and simultaneously the fat signal distribution at the same spatial resolution. For this purpose, for example a three-point Dixon technique may be employed. In the Dixon reconstruction, further the fat spectrum may be modelled to improve the water-fat separation.

By employing a multi-echo Dixon acquisition technique, nevertheless the total data acquisition time has to be kept at an acceptable level. Thus, instead of performing multiple separate MR data acquisition processes with each process being used for acquiring coronary magnetic resonance angiography datasets at a different echo time, a multi-echo Dixon acquisition approach is employed which can be tuned in such a manner that the total data acquisition time compared to state of the art coronary magnetic resonance angiography is only extended by less than 30% for certain field strength and protocols. Additionally, in order to further decrease the scan time parallel imaging may be applied.

In accordance with a further embodiment of the invention, the multi-echo Dixon acquisition comprises employing a gradient echo-type, balanced fast field echo-type pulse sequence or a fast spin echo-type sequence. This has the advantage, that the repetition rate for data acquisition can be further increased. Less refocusing pulses are required in a given timeframe in order to achieve a reliable separation of image data of water and fat based on the acquired echo data.

In accordance with a further embodiment of the invention, the method further comprises employing a magnetization transfer contrast sequence (MTC). For example, an MTC-based magnetization preparation may be used which maintains the desired blood-myocardium contrast, but does not have any impact on the fat. Fat shows no MTC effect. This permits to improve the contrast between blood and myocardium without reducing the amplitude of the fat signal and thus reducing the fat signal to noise ratio (SNR), making quantification performed subsequently more difficult. Further, outer volume suppression may be used to avoid signals folded in from areas exposed to different main magnetic fields. The entire measurement is performed using conventional navigator gating and ECG triggering to avoid respiratory and cardiac motion artefacts.

In accordance with a further embodiment of the invention, the datasets are acquired using spiral or radial imaging. For example spiral imaging embedded in a clinical shift encoding approach permits the separation of chemical shifts from $\Delta B_0$ induced off-resonance artefacts. In this way water and fat signals can be sepeated and due to the main field inhomogeneity map, estimated by the Dixon separation, additionally image deblurring, off-resonance correction, can be performed for non-Cartesian water/fat resolved imaging.

In accordance with a further embodiment of the invention, the datasets are acquired in the k-t space employing undersampling, wherein the processing of the datasets comprises compressed sensing (CS). This further permits to compensate for the additional time needed for chemical shift encoding. Compressed sensing is for example known from Lustig et al., 'The Application of Compressed Sensing for Rapid MR Imaging', Magnetic Resonance in Medicine 2007, 58(6) column 118-95. By extending this CS k-space undersampling concept to the application of undersampling in k and time (t) space, the total data acquisition process can further be sped up in a considerable way.

In accordance with a further embodiment of the invention, the method further comprises processing the water image data for extraction of myocardial contour data, applying the extracted myocardial contour data to the fat image data and performing a myocardial fat infiltration analysis. The data can further be used to investigate or identify areas in which fatty tissue is present of represents a marker for disease or malfunction.

In another aspect, the invention relates to a magnetic resonance imaging apparatus for performing coronary magnetic resonance angiography with signal separation for water and fat, wherein the apparatus comprises a magnetic resonance imaging scanner for acquiring magnetic resonance image data, a controller adapted for controlling a scanner operation for acquiring coronary magnetic resonance angiography datasets using multi-echo Dixon acquisition and a data reconstruction system adapted for processing the datasets for reconstruction of a first and second image dataset, the first and second image dataset comprising separate water and fat image data, wherein the processing of the datasets comprises a Dixon reconstruction technique.

In accordance with an embodiment of the invention, the controller is further adapted for controlling the scanner operation for acquiring the datasets in the k-t space employing undersampling, wherein the data reconstruction system is adapted for processing of the datasets employing compressed sensing.

The method of the invention can be advantageously carried out in most MR devices in clinical use at present. To this end, it is merely necessary to utilize a computer program by which the MR device is controlled such that it performs the above explained method steps of the invention. The computer program may be either present on a data carrier or be present in a data network so as to be downloaded for installation in the control unit of the MR device. Therefore, the invention also relates to a computer program product comprising computer executable instructions to perform the method as described above.

The enclosed drawings disclose preferred embodiments of the present invention. It should be understood, however, that the drawings are designed for the purpose of illustration only and not as a definition of the limits of the invention.

DETAILED DESCRIPTION OF EMBODIMENTS

Figure 1:
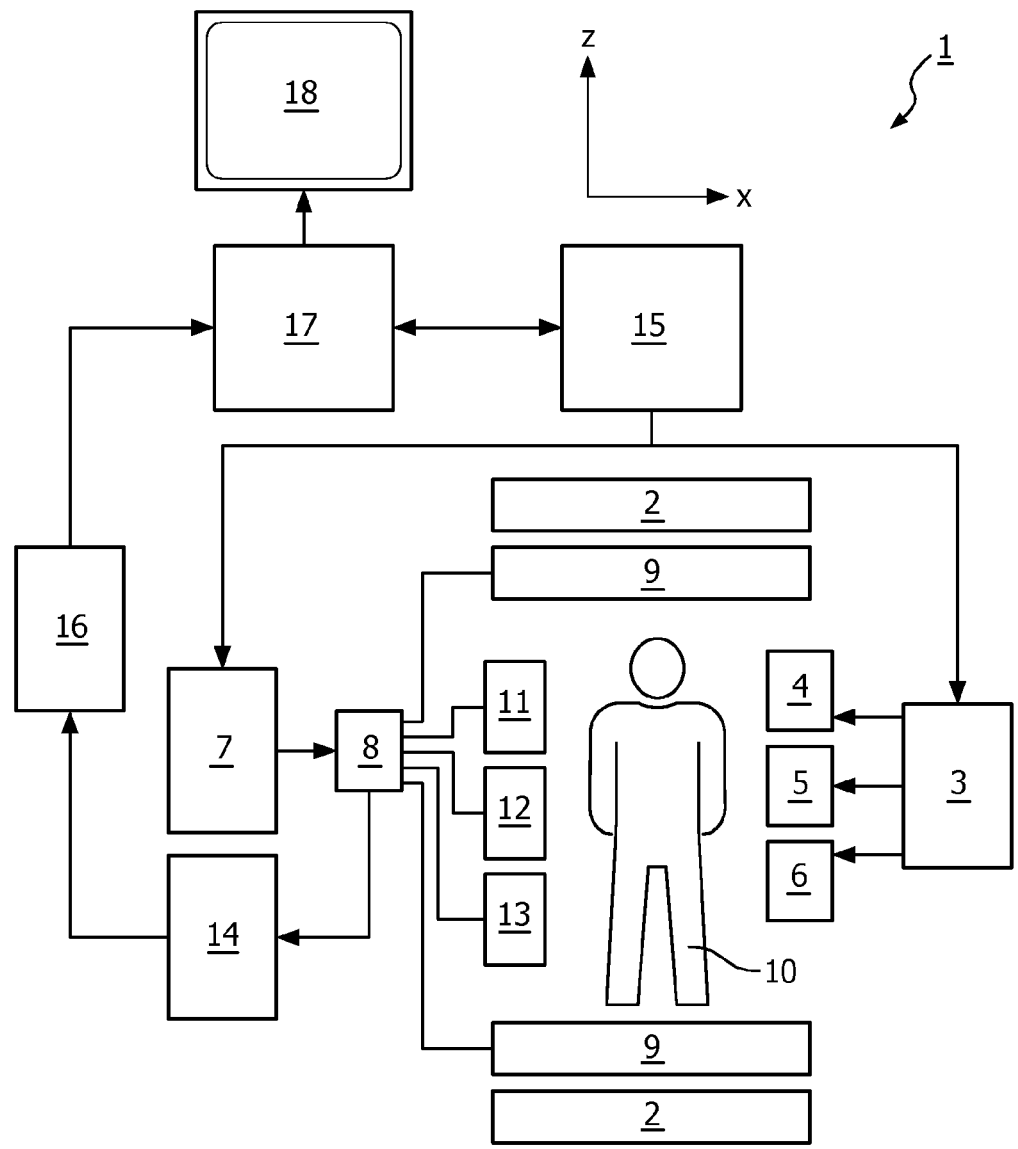
FIG. 1 shows an MR device for carrying out the method of the invention.

In the following similar elements are denoted by the same reference numerals.

With reference to FIG. 1, an MR imaging system 1 is shown. The system comprises superconducting or resistive main magnet coils 2 such that a substantially uniform, temporarily constant main magnetic field $B_0$ is created along a z-axis through an examination volume.

A magnetic resonance generation manipulation system applies a series of RF pulses and switched magnetic field gradients to invert or excite nuclear magnetic spins, induce magnetic resonance, refocus magnetic resonance, manipulate magnetic resonance, spatially or otherwise encode the magnetic resonance, saturate spins and the like to perform MR imaging.

More specifically, a gradient pulse amplifier 3 applies current pulses to selected ones of whole body gradient coils 4, 5 and 6 along x, y and z-axes of the examination volume. An RF transmitter 7 transmits RF pulses or pulse packets, via a send/receive switch 8 to an RF antenna 9 to transmit RF pulses into the examination volume. A typical MR imaging sequence is composed of a packet of RF pulse sequences of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals may also be picked up by the RF antenna 9.

For generation of MR images of limited regions of the body or in general object 10, for example by means of parallel imaging, a set of local array RF coils 11, 12 and 13 are placed contiguous to the region selected for imaging. The array coils 11, 12 and 13 can be used to receive MR signals induced by RF transmissions effected via the RF antenna. However, it is also possible to use the array coils 11, 12 and 13 to transmit RF signals to the examination volume.

The resultant MR signals are picked up by the RF antenna 9 and/or by the array of RF coils 11, 12 and 13 and are demodulated by a receiver 14 preferably including a preamplifier (not shown). The receiver 14 is connected to the RF coils 9, 11, 12 and 13 via a send/receive switch 8.

A host computer 15 controls the gradient pulse amplifier 3 and the transmitter 7 to generate any of a plurality of imaging sequences, such as echo planar imaging (EPI), echo volume imaging, gradient and spin echo imaging, fast spin echo imaging, CMRA imaging and the like. For the selected sequence, the receiver 14 receives a single or a plurality of MR data lines in a rapid succession following each RF excitation pulse. A data acquisition system 16 performs analogue to digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, like for example Dixon reconstruction and compressed sensing. The MR image may represent a planar slice through the patient, an array of parallel planar slices, a three-dimensional volume or the like. The image is then stored in an image memory where it may be accessed for converting slices or other portions of the image representation into appropriate formats for visualization, for example via a video monitor 18 which provides a man readable display of the resultant MR image.

Figure 2A:
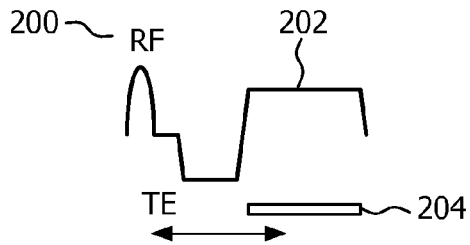
FIG. 2 illustrates the replacement of a standard Dixon data acquisition process with a multi-echo sampling process.
Figure 2B:
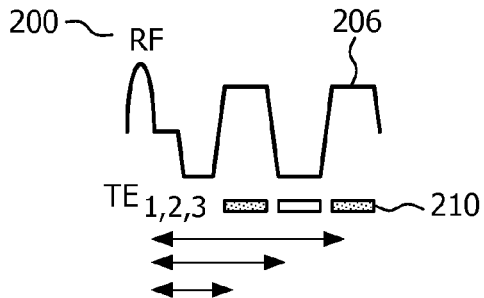

FIG. 2 illustrates the replacement of a state of the art readout process (FIG. 2a) by means of a multi-echo Dixon acquisition technique (FIG. 2b). In FIG. 2a, a respective excitation 200 is followed by the application of a readout gradient 202, wherein at the same time for acquiring an echo at echo time TE a signal sampling 204 is performed for an appropriate period of time.

In FIG. 2B, an oscillating readout gradient 206 is used for the generation of multiple echoes in order to perform a multi-echo Dixon acquisition. The readout gradient 206 has different polarities to encode the chemical shift information efficiently. Further, a signal sampling 210 is performed in three subsequent steps in time, wherein each signal sampling step corresponds to a given echo time $TE_{1,\,2,\,3}$ of the multiple echoes generated by the oscillating read gradient 206.

The three echo sampling process is using a higher bandwidth than the single echo of FIG. 2a resulting nevertheless in a comparable repetition time and also a comparable signal sampling time per unit time (which is proportional to the SNR). As can be seen from FIG. 2b, the total repetition time (TR) is only marginally lengthened compared to the acquisition used in FIG. 2a. The approach of FIG. 2b has the advantage that all chemical shift encoded echoes experience the same spin history, with respect to all kind of effects (motion, etc), which otherwise might result in artifacts during the Dixon reconstruction.

Figure 3:
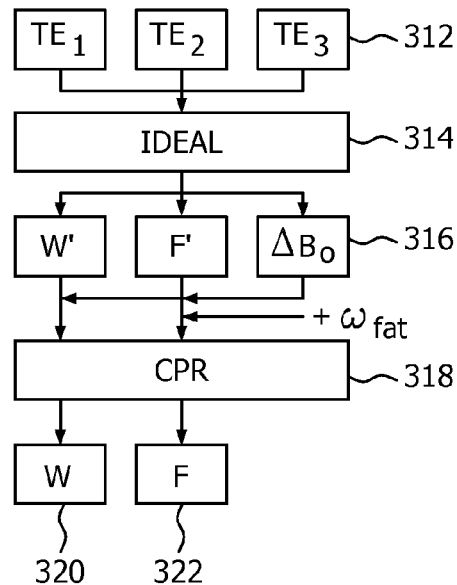
FIG. 3 illustrates a three-point Dixon water-fat separation and off resonance correction.
Figure 3:
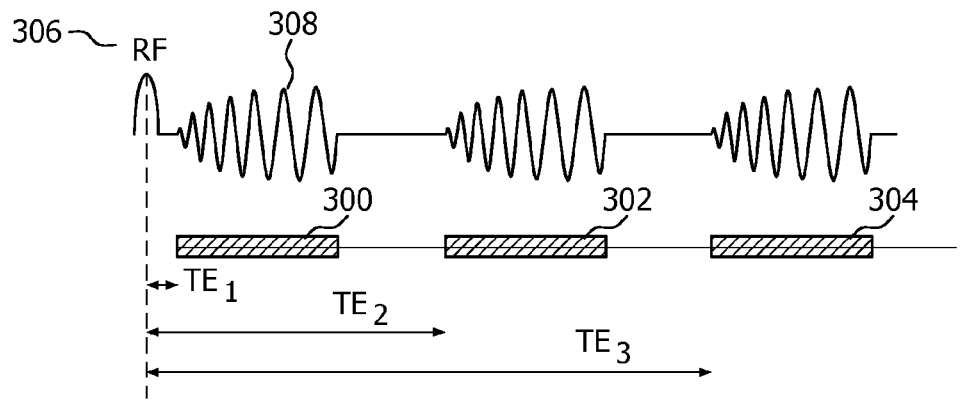

FIG. 3 illustrates a three-point Dixon water-fat separation and off-resonance correction. For example a spiral or radial imaging sequence may be used, embedded in the chemical shift encoding approach. This allows separating chemical shifts from $\Delta B_0$, additionally facilitating off resonance corrected non-Cartesian water/fat resolved imaging. Spiral gradient echo imaging may be performed using chemical shift encoding employing a fixed k-space trajectory, which may be shifted in time to sample three individual echoes. However, as mentioned above preferably a multi-echo approach may also be used here.

In case spiral gradient echo imaging is performed using chemical shift encoding employing a fixed k-space trajectory which is shifted in time to sample three individual echoes (300, 302 and 304), after magnetization preparation the magnetization prepared with the excitation 306 is read out using a gradient echo train 308 consisting of multiple spiral interleaves using a flip angle sweep ensuring that the last shot tips down or longitudinal magnetization is still available.

In case of coronary imaging, a heartbeat gating may be applied such that in the next heartbeat the same interleaves are sampled with an incremented TE, followed by a data acquisition in the next heartbeat of the corresponding $2\times\Delta TE$ encoded data. Real time navigator gating with perspective motion correction using for example a rigid body motion model and heartbeat gating may be applied acquiring the data in mid/late diastole resulting in a scan time of about for example 8 minutes in the case of a 50% gating efficiency and a $\Delta TE$ of 1.5 milliseconds in a 1.5 Tesla system. Parallel imaging may be further used to partly compensate for a longer scan time of three-point Dixon imaging. Further, a phase-conserving unfolding operation may lead to a significant reduction in computational complexity because it merges all multi-channel data into a single image.

On the right hand side of FIG. 3 a Dixon reconstruction process is illustrated which holds for both, Dixon imaging with individual echoes at different echo times as well as multi-echo Dixon acquisition. In step 312, image data resulting from the acquisition of coronary magnetic resonance angiography datasets using multi-echo Dixon acquisition is input to the Dixon reconstructing module, wherein each $TE_n$ corresponds to a different echo time. In step 314 the data is processed resulting in step 316 in a preliminary water image dataset, a preliminary fat image dataset as well as a $\Delta B_0$ map.

By an additional conjugated phase reconstruction step in step 318 optimized water image data (320) and fat image data (322) is obtained.

As mentioned above, when acquiring the coronary magnetic resonance angiography datasets using the multi-echo Dixon acquisition, the datasets may be acquired in the k-t space employing undersampling, wherein the processing of the datasets comprises compressed sensing. Compressed sensing allows signal reconstruction from a small set of random linear measurements by exploiting signal sparsity. Assuming that a signal is sparse in some known transform domain, the sparsest solution agreeing with the given measurements is with very high probability the correct solution. In detail, compressed sensing (CS) suggests that a sparse discrete signal x of length m with at most v non-zero components can be reconstructed from n linear measurements (samples), where n is a small multiple of v. The measurement vector y can be described as $$y = \Phi x + \eta; \quad (1)$$

where $\Phi$ is the measurement matrix, x is the signal of interest and $\eta$ is a noise vector. If the number of samples n is less than m, this is an underdetermined linear system with an infinite number of solutions. The main statement of CS is that, if the signal is sparse in some transform domain, it can be reconstructed from substantially less than m measurements by a non-linear reconstruction procedure.

One possible method for sparse data recovery is by means of L1 minimization. The signal can be recovered by solving the convex optimization problem $$\min \|\Psi x\|_1, \text{subject to } \|Fx - y\|_2^2 < \epsilon \quad (2)$$

where y is the measurement vector, x is the signal to be recovered, F is the measurement or encoding matrix, $\Psi$ is the sparsifying transform, and the parameter $\epsilon$ is related to the noise level. Finite differences and wavelets are commonly used as a sparsifying transform.

One approach to combine CS and water-fat separation is to perform CS reconstruction on each individual echo data set and to perform the water-fat separation in a second step. This approach may be convenient because the CS reconstruction is independent of the water-fat separation method. Furthermore, in such decoupled reconstruction the water-fat separation is performed on the data obtained from the CS reconstruction and does not have reference to the original data.

Therefore, coronary magnetic resonance angiography datasets may be acquired using multi-echo Dixon acquisition and subsequent CS reconstruction which in a fast and reliable manner provides a good visibility of coronaries on reconstructed MR images and at the same time valuable information on fibro-fatty infiltration of the myocardium. It has to be noted that the CS reconstruction approach may be also combined with parallel imaging in order to further speed up the data acquisition process. This way, the total scanning time can further be reduced.

It has to be further noted, that instead of the above mentioned three-point Dixon approach also a two-point Dixon approach may be used to further accelerate the sampling process.

The invention claimed is:

1. A method of performing coronary magnetic resonance angiography with signal separation for water and fat, the method comprising:

acquiring coronary magnetic resonance angiography three-dimensional datasets in k-space with individual echoes at different echo times from an excitation using multi-echo Dixon acquisition;

processing the datasets for reconstruction of a first and second three-dimensional image datasets in image space, the first and second image datasets comprising separate water and fat image data, respectively, wherein the processing of the datasets comprises a Dixon reconstruction technique by processing the water image data for extraction of myocardial contour data and applying the extracted myocardial contour data to the fat image data; and employing a magnetization transfer contrast sequence.

2. The method of claim 1, wherein the datasets in three-dimensional k-space are acquired in the k-t space employing undersampling, wherein the processing of the datasets comprises compressed sensing.

3. A method of performing coronary magnetic resonance angiography with signal separation for water and fat, the method comprising:

acquiring coronary magnetic resonance angiography three-dimensional datasets in k-space with individual echoes at different echo times from an excitation using multi-echo Dixon acquisition; and processing the datasets for reconstruction of a first and second three-dimensional image datasets in image space, the first and second image datasets comprising separate water and fat image data, respectively, wherein the processing of the datasets comprises a Dixon reconstruction technique by processing the water image data for extraction of myocardial contour data and applying the extracted myocardial contour data to the fat image data; wherein the three-dimensional datasets in k-space are acquired using spiral or radial imaging.

4. The method of claim 1, wherein the multi-echo Dixon acquisition comprises employing a gradient-echo, balanced fast field echo pulse sequence or a Fast Spin Echo sequence.

5. The method of claim 1, further comprising: performing a myocardial fat infiltration analysis.

6. A computer program product comprising computer executable instructions stored in non-transitory computer readable medium to perform the method steps as claimed in claim 1.

7. A magnetic resonance imaging apparatus for performing coronary magnetic resonance angiography with signal separation for water and fat, the apparatus comprising:

a magnetic resonance imaging scanner for acquiring magnetic resonance image data;

a controller adapted for controlling a scanner operation of acquiring coronary magnetic resonance angiography three-dimensional datasets in k-space with individual echoes at different echo times from an excitation using multi-echo Dixon acquisition; and a data reconstruction system adapted for processing the three-dimensional datasets in k-space for reconstruction of a first and second three-dimensional image data set in image space, the first and second image data set comprising separate water and fat image data, wherein the processing of the datasets comprises a Dixon reconstruction technique, wherein the controller is further adapted for controlling the scanner operation for acquiring the three-dimensional datasets in the k-t space employing undersampling, wherein the data reconstruction system is adapted for processing of the datasets employing compressed sensing.

8. The method of claim 1, wherein an oscillating readout gradient is used for generating the plurality of echoes in order to perform the multi-echo Dixon acquisition.

* * * * *